United States Patent [19]

Giolito et al.

[11] 4,042,514
[45] Aug. 16, 1977

[54] NOVEL LUBRICATING COMPOSITIONS CONTAINING DERIVATIVES OF 1,2-DITHIOL-3-THIONES OR 1,2-DITHIOL-3-ONES

[75] Inventors: Francois Giolito, Lyon; Georges Rivier, Bron, both of France

[73] Assignee: Orogil, Paris, France

[21] Appl. No.: 655,482

[22] Filed: Feb. 5, 1976

[30] Foreign Application Priority Data

Feb. 17, 1975 France .................................. 75.04796

[51] Int. Cl.² .............................................. C10M 1/38
[52] U.S. Cl. ..................................... 252/48.6; 252/45; 252/48.4
[58] Field of Search ........................ 252/45, 48.4, 48.6

[56] References Cited

U.S. PATENT DOCUMENTS

| 2,653,910 | 9/1953 | Airs et al. ............................. 252/45 |
| 2,816,075 | 12/1957 | Fields ..................................... 252/45 |
| 2,995,569 | 8/1961 | Hamilton et al. ................... 252/45 X |
| 3,062,833 | 11/1962 | Boberg et al. ................... 252/48.4 X |
| 3,345,380 | 10/1967 | Hodgson ........................... 252/45 X |
| 3,350,408 | 10/1967 | Hodgson ........................... 252/45 X |
| 3,364,232 | 1/1968 | Anderson .......................... 252/45 X |

Primary Examiner—Delbert E. Gantz
Assistant Examiner—Andrew H. Metz

[57] ABSTRACT

Novel lubricating compositions are provided comprising at least one lubricating oil and at least one derivative of 1,2-dithiol-3-thiones or 1,2-dithiol-3-ones, carrying a 5-alkylthio or 5-alkarylthio substituent. The novel compositions are prepared by mixing the constituents. The novel lubricating compositions find application as oils for engines, gearboxes, automatic transmissions and the like.

5 Claims, No Drawings

NOVEL LUBRICATING COMPOSITIONS CONTAINING DERIVATIVES OF 1,2-DITHIOL-3-THIONES OR 1,2-DITHIOL-3-ONES

BACKGROUND OF THE INVENTION

The present invention relates to novel lubricating compositions.

It has been proposed (U.S. Pat. No. 2,653,910, No. 2,995,569 and No. 3,673,090) to improve the extreme-pressure properties, antioxidant properties and antiwear properties of lubricating oils by means of additives based on alkyl- or aryldithiol-thiones obtained by sulphurization of polyisobutene.

Although among such additives some perform well, they, however, suffer from the disadvantage of being of limited solubility in mineral oils, of having a disagreeable odor and of imparting an intense color to the oil and to the skin. These additives must be handled with care, particularly if they are used in oils employed in metal-working.

It is an object of the present invention to provide a lubricating composition which does not have the shortcomings of the prior art.

It is also an object of the present invention to provide lubricating compositions containing additives and which provide improved properties.

Other objects of the invention will be apparent to those skilled in the art from the present description.

GENERAL DESCRIPTION OF THE INVENTION

By the present invention, it has been found that the derivatives of the 1,2-dithiol-3-thiones or 1,2-dithiol-3-ones which carry an alkylthio or alkylarylthio substituent do not suffer from the disadvantages of the prior art additives. In addition to having extremely good pressure properties at least equal to those of alkyl- or aryl-dithiol-thiones, and good heat stability, they are efficient agents for protecting bearings. The derivatives of the invention can, in particular, be used as additives in oils for engines, gearboxes and fluid drives and for oils used in the mechanical engineering industries.

The novel lubricating compositions of the invention comprise at least one lubricating oil and at least one additive derived from the 1,2-dithiol-3-thiones or 1,2-dithiol-3-ones characterized in that the said derivative has the formula

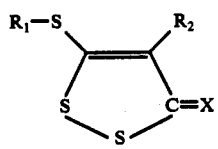

in which formula $R_1$ is an optionally substituted alkyl radical or an optionally substituted alkylaromatic radical, $R_2$ is a hydrogen atom, an optionally substituted alkyl radical, a halogen atom, or a carboxyalkyl radical COOR in which R is an alkyl radical containing from about 1 to 12 carbon atoms, $R_1$ and $R_2$ together having a total of from about 3 to 24 carbon atoms when $R_2$ is a hydrogen atom, an alkyl or carboxyalkyl radical, and $R_1$ having from about 2 to 22 carbon atoms when $R_2$ is a halogen atom, and X is a sulphur atom, regardless of the nature of the radicals $R_1$ $R_2$, or is an oxygen atom when $R_2$ is a halogen atom.

The preferred lubricating compositions of the invention are those in which $R_1$ and $R_2$ together have from about 5 to 24 carbon atoms in total when $R_2$ is an alkyl or carboxyalkyl radical, those in which $R_1$ contains from about 5 to 19 carbon atoms when $R_2$ is a hydrogen atom and those in which $R_1$ has from about 3 to 13 carbon atoms when $R_2$ is a chlorine atom.

The lubricating oils present in the said compositions can be oils having a viscosity of between about 20.6 and 541 centistokes at 37.8° C. [100 to 2,500 SUS (Saybolt Universal Viscosity) at 100° F.], including natural oils, synthetic, or semi-synthetic bases (synthetic hydrocarbons, esters, polyesters and polyethers) of comparable viscosity.

Among the additives which can be present in the said compositions there may be mentioned, by way of example: 5-n-butylthio-4-methyl-1,2-dithiol-3-thione, 5-hyptylthio-4-methyl-1,2-dithiol-3-thione, 5-dodecylthio-4-methyl-1,2-dithiol-3-thione, 5-dodecylbenzylthio-4-neopentyl-1,2-dithiol-3-thione, 5-n-pentylthio-4-H-1,2-dithiol-3-thione, 5-para-dodecylbenzylthio-4-H-1,2-dithiol-3-thione, 5-t-butylthio-4-chloro-1,2-dithiol-3-thione, 5-dodecylthio-4-chloro-1,2-dithiol-3-thione, 5-p-methylbenzylthio-4-chloro-1,2-dithiol-3-thione, 5-n-hexylthio-4-carbohexoxy-1,2-dithiol-3-thione, 5-hexylbenzylthio-4-carbohexoxy-1,2-dithiol-3-thione, 5-t-butylthio-4chloro-1,2-dithiol-3-one, 5-isopropylthio-4-chloro-1,2-dithiol-3-one and 5-hexylbenzylthio-4-chloro-1,2-dithiol-3-one.

The 5-alkyl- or 5-alkaryl-thio-4-H-1,2-dithiol-3-thiones can be prepared by sulphurization of 1,2-dithiol-3-thione with sulphur and hydrogen sulfide in the presence of dimethylformamide, followed by an alkylation of the dimethylammonium salt formed by means of an alkyl halide or alkaryl halide.

The 5-alkyl- or 5-alkaryl-thio-4-alkyl-1,2,dithiol-3-thiones can be prepared by sulphurization of 5-H-4-alkyl-1,2-dithiol-3-thiones with sulphur and hydrogen sulfide in the presence of dimethylformamide, followed by an alkylation of the dimethylammonium salt formed by means of an alkyl halide or alkaryl halide.

The 5-alkyl- or 5-alkaryl-thio-4-carbalkoxy-1,2-dithiol-3-thiones can be prepared by sulphurization of 5-H-4-carbalkoxy-1,2-dithiol-3-thiones with sulphur in the presence of dimethylformamide, followed by an alkylation of the dimethylammonium salt formed by means of an alkyl halide or alkaryl halide.

The 5-alkyl- or 5-alkaryl-thio-4-chloro-1,2-dithiol-3-ones can be prepared by reaction of an alkyl-mercaptan or alkaryl-mercaptan with 4,5-dichloro-1,2-dithiol-3-one in a benzene medium and in the presence of pyridine. The action of $P_4S_{10}$ on these products leads to the formation of 5-alkyl- or 5-alkaryl-thio-4-chloro-1,2-dithiol-3-thione.

The amounts of additives of the invention which can be introduced into the compositions which form the subject of the invention are between 0.2 and 10% and preferably between 0.2 and 5% by weight of the said composition. These amounts of additives depend on the future use of the compositions, namely, whether they are used as oils for engines, gearboxes or automatic transmissions, as a hydraulic fluid or as a cutting oil for the mechanical engineering industry.

The compositions of the invention can also contain anti-oxidant, anti-corrosion, anti-foaming or detergent-dispersing adjuvants, without causing a problem connected with compatibility or a deterioration in the level of performance.

The said compositions which form the subject of the invention can be prepared by dissolving the additive in the base oil or, if other adjuvants are to be present, by dissolving the additive in the base oil to which the said adjuvants have been added or by dissolving the additive in the said adjuvants and adding the base oil.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, the throughout the specification, the quantities of material are expressed in terms of parts by weight, unless otherwise specified.

EXAMPLE 1

Preparation of
5-n-butylthio-4-methyl-1,2-dithiol-3-thione 250 grams (g.) of 4-methyl-1,2-dithiol-3-thione and 84 g. of sulphur were dissolved in 2.5 liters of dimethylformamide. The resulting solution was kept for 14 hours at the reflux temperature of dimethylformamide, while constantly bubbling hydrogen sulfide through the solution. The dimethylformamide was then removed by means of a rotary evaporator; the solid product obtained was taken up in 2liters of toluene. The resulting toluene solution was kept for 24 hours at about minus 15° C., during which time 200 g. of 5-dimethylammoniumthio-4-methyl-1,2-dithiol-3-thione precipitated from the toluene, representing a yield of 53%.

Thereafter, 180 g. of the product obtained were dissolved in 2 liters of ethanol and 120 g. of butyl bromide were then run in slowly. The temperature was kept at 60°-70° C. for ¾ hour. After cooling, the precipitate obtained was filtered off and then dissolved in 1 liter of benzene; the filtrate was concentrated by evaporation so as to remove the ethanol. The residue obtained by concentration was taken up in benzene and the rusulting solution was then filtered. The two benzene solutions were combined and then concentrated by evaporation. This gave 160 g. of crude 5-n-butylthio-4-methyl-1,2-dithiol-3-thione, which represents a yield of 85%.

The product was purified by recrystallization from 1.5 liters of ethanol; this gave 142 g. of a brown-yellow product of melting point between 6° and 61° C.

EXAMPLE 2

Following the working method described in Example 1, 5-heptylthio-4-methyl-1,2-dithiol-3-thione was prepared by sulphurization of 4-methyl-1,2-dithiol-3-thione, followed by alkylation of the 5-dimethylammoniumthio-4-methyl-1,2-dithiol-3-thione with heptyl bromide.

The resulting 5-heptylthio-4-methyl-1,2-dithiol-3-thione was and orange crystalline product.

EXAMPLE 3

Following the working method described in Example 1, 5-dodecylthio-4-methyl-1,2-dithiol-3-thione was prepared by sulphurization of 4-methyl-1,2-dithiol-3-thione, followed by alkylation of the 5-dimethylammoniumthio-4-methyl-1,2-dithiol-3-thione with dodecyl bromide.

The resulting 5-dodecylthio-4-methyl-1,2-dithiol-3-thione was a yellow crystalline product of melting point 57° C.

EXAMPLE 4

Preparation of
5-dodecylbenzylthio-4-neopentyl-1,2-dithiol-3-thione 20.5 g (1/10 mol) of 5-H-4-neopentyl,1,2-dithiol-3-thione were dissolved in 300 ml. of dimethylformamide. 3.2g. of sulphur were introduced and the mixture was heated at the reflux temperature for 14 hours, with hydrogen sulfide bubbling through. The dimethylformamide was driven off by evaporation; the residue was taken up in a mixture of benzene and petroleum ether. The resulting solution was kept cold for 48 hours. The dimethylammonium salt precipitated (10 g., representing a yield of 33%) and was isolated and then dissolved in 100 ml. of ethyl alcohol. The resulting solution was heated to the reflux temperature and 10 g. of dodecylbenzyl chloride were run in slowly; the mixture was allowed to react for ½ hour. The solution obtained was concentrated and the residue was taken up in benzene. The ammonium hydrochloride which precipitated was removed and the filtrate was then concentrated by evaporation. 15 g. of a red oil were obtained and were purified by chromatography. 13 g. of 5-dodecylbenzylthio-4-neopentyl-1,2-dithiol-3-thione (representing a yield of 27%) were thus obtained.

EXAMPLE 5

Preparation of 5-n-pentylthio-4-H-1,2-dithiol-3-thione 33.5 g. of 1,2-dithiol-3-thione (¼ mol) were dissolved in 350 ml. of dimethylformamide. 8 g. of sulphur (¼ mol) were introduced and the resulting mixture was then heated at the reflux temperature for 14 hours while constantly bubbling hydrogen sulfide through it. The dimethylformamide was removed by distillation in vacuo. The residue was taken up in a mixture of toluene and petroleum ether and then kept cold for 24 hours. 27 g. of dimethylammonium salt then precipitated (50% yield), were filtered, and the filtered solid dissolved in ethyl alcohol. The resulting solution was heated to the reflux temperature and 20 g. of n-pentyl bromide were added dropwise. The alcohol solution was concentrated by evaporation and the residue was taken up in benzene. Dimethylammonium hydrobromide precipitated from the benzene and was removed by filtration, and the filtrate was then concentrated by evaporation.

18 g. (60% yield) of crude 5-n-pentylthio-4-H-1,2-dithiol-3-thione were obtained and after recrystallization from ethanol, 17 g. (55% yield) of pure product were obtained.

EXAMPLE 6

Preparation of
5-para-dodecylbenzylthio-4-H-1,2-dithiol-3-thione 6.3 g. of 5-dimethylammoniumthio-4-H-1,2-dithiol-3-thione (3/100 mol), prepared according to the method described in Example 5, were dissolved in 50 ml. of ethanol, and 3/100 mol of p-dodecylbenzyl chloride were then run in. The mixture was allowed to react for 1 hour at the boiling point. The resulting solution was then concentrated by evaporation and the residue was taken up in benzene. Dimethylammonium hydrochloride precipitated from the benzene. After filtration, the filtrate was concentrated. After recrystallization, 4 g. of pure 5-paradodecybenzylthio-4-H-1,2-dithiol-3-thione (31% yield) were obtained.

EXAMPLE 7

Preparation of 5-butylthio-4-chloro-1,2-dithiol-3-one 374 g. (2 mols) of 4,5-dichloro-1,2-dithiol-3-one were dissolved in 3 liters of benzene, 160 g. (2 mols) of pyridine were introduced and 180 g. (2 mols) of t-butylmercaptan are run in over the course of 1 hour while keeping the temperature constant at 20° C. As soon as the first drops of t-butylmercaptan were introduced, a precipitate of pyridinium hydrochloride appeared, and the temperature was kept at 20° C. for 1 hour. The precipitate of pyridinium hydrochloride was filtered off and the filtrate was concentrated by means of a rotary evaporator. The residue was recrystallized from 3 liters of ethanol.

This gave 360 g. of 5-t-butylthio-4-chloro-1,2-dithiol-3-one (corresponding to a yield of 75%) in the form of a brownyellow product, having a melting point of 49° C.

EXAMPLE 8

Preparation of 5-isopropylthio-4-chloro-1,2-dithiol-3-one

5-Isopropylthio-4-chloro-1,2-dithiol 3-one was prepared in accordance with the method described in Example 7, by reaction of isopropylmercaptan with 4,5-dichloro-1,2-dithiol-3-one.

5-Isopropylthio-4-chloro-1,2-dithiol-3-one is a light yellow crystalline product having a melting point of 60° C.

EXAMPLE 9

Preparation of 5-hexylbenzylthio-4-chloro-1,2-dithiol-3-one 5.8 g. of hexylbenzylmercaptan were run slowly into a solution containing 5.61 g. of 5,4-dichloro-1,2-dithiol-3-one (3/100 mol), 2.4 g. of pyridine and 50 ml. of benzene, while keeping the temperature at 10°-15° C. The pyridinium hydrochloride formed was filtered off after a reaction time of ¼ hour. The filtrate was concentrated by evaporation. The residue was treated with animal charcoal in ethyl alcohol for 1 hour. After filtering, and removing the alcohol by evaporation, 7 g. (70% yield) of 5-hexylbenzylthio-4-chloro-1,2-dithiol-3-one were obtained in the form of a yellow crystalline product.

EXAMPLE 10

Preparation of 5-t-butylthio-4-chloro-1,2-dithiol-3-thione 11 g. of crystals of 5-t-butylthio-4-chloro-1,2-dithiol-3-one prepared in Example 7 were dissolved in xylene, together with an excess of $P_4S_{10}$; the mixture was allowed to react for 3-4 hours at the boiling point. After washing and removing the solvent, a red oil was obtained and was chromatographed. After evaporating the eluant, 4 g. of 5-butylthio-4-chloro-1,2-dithiol-3-thione of melting point 45° C. were obtained.

EXAMPLE 11

Preparation of 5-dodecylthio-4-chloro-1,2-dithiol-3-thione 3.74 g. (2/100 mol) of 4,5-dichloro-1,2-dithiol-3-one were introduced slowly into a mixture consisting of 50 ml. of benzene, 1.60 g. (2/100 mol) of pyridine and 4.04 g. (2/100 mol) of dodecylmercaptan. The temperature was kept at 10°-15° C. during the period of the introduction. The pyridinium hydrochloride formed was filtered off after a reaction time of ¼ hour. The filtrate was concentrated and a red oil was obtained, which crystallized in the cold. After recrystallization from ethanol, 5.2 g. of white crystals of 5-dodecylthio-4-chloro-1, 2-dithiol-3-one were obtained. These crystals were dissolved in 50 ml. of xylene together with an excess of $P_4S_{10}$. The resulting mixture was allowed to react for 1 hour at the boiling point. After washing with a solution of sodium bicarbonate until a neutral pH was obtained, the organic phase was dried over calcium chloride and then concentrated by evaporation. The resulting residue was chromatographed on alumina using an eluant mixture of benzene and petroleum ether. After removing the solvents, 2.6 g. of pure 5-dodecylthio-4-chloro-1,2-dithiol-3-thione (33% yield) were obtained.

EXAMPLE 12

Preparation of 5-p-methylbenzylthio-4-chloro-1,2-dithiol-3-thione 5.5 g. of methylbenzylmercaptan were run slowly into a benzene solution containing 7.5 g. (4/100 mol) of 4.5-dichloro-1,2-dithiol-3-one, 3.6 g. of pyridine and 50 ml. of benzene, while maintaining the temperature at 10° C. After removing the pyridinium hydrochloride, the filtrate was concentrated by evaporation. The residue was taken up in 70 ml. of xylene and 14 g. of $P_4S_{10}$ were then added. The resulting mixture was refluxed for 1 hour. After washing until a neutral pH was obtained, the organic phase was dried and concentrated. A red oil was obtained and this was chromatographed. After evaporating the eluant, 4 g. (35% yield) of 5-p-methylbenzylthio-4-chloro-1,2-dithiol-3-thione were obtained in the form of a red crystalline product.

EXAMPLE 13

Preparation of 5-n-hexylthio-4-carbohexoxy-1,2-dithiol-3-thione 10.50 g. (4/100 mol) of 5-H-4-carbohexoxy-1,2-dithiol-3-thione (prepared by sulphurization of hexyl methacrylate in accordance with the process described in U.S. Pat. No. 3,394,146) were dissolved in 50 ml. of dimethylformamide. 2 g. of sulphur were introduced and the mixture was refluxed for 14 hours. The dimethylformamide was driven off and 5 g. (40% yield) of an oil were obtained. This oil was dissolved in 100 cc. of ethanol. 3.3 g. of hexyl bromide were then run in and the mixture was refluxed for 1-2 hours. The alcohol and the dimethylammonium hydrobromide were removed. The residue was chromatographed on alummina with an eluant mixture of benzene and petroleum ether. After evaporating the solvents, 4.7 g. (30% yield) of 5-n-hexylthio-4-carbohexoxy-1,2-dithiol-3-thione were obtained in the form of a red crystalline product.

EXAMPLE 14

Preparation of 5-hexylbezylthio-4-carbohexoxy-1,2-dithiol-3-thione 10 g. (1/30 mol) of a dimethylammonium salt were prepared in accordance with the method described in Example 13, by sulphurization of 5-H-4-carbohexoxy-1,2-dithiol-3-thione in dimethylformamide. This salt was dissolved in 200 ml. of ethanol. The mixture was refluxed and 10 g. of hexylbenzyl chloride were run in slowly. This resulting mixture was allowed to react for ½ hour, the alcohol was removed and the residue was then taken up in benzene. Dimethylammonium hydrochloride precipitated and was filtered off, and the filtrate was then concentrated by evaporation. The residue was chromatographed. After evaporating the eluants, 6.2 g. (40% yield) of 5-hexylbenzylthio-4-carbohexoxy-1,2-dithiol-3-thione were obtained.

EXAMPLE 15

A lubrocating composition was prepared by adding 1% of the product obtained in Example 1 to a lubricating mixture consisting of an SAE 30 base mineral oil containing 5% by weight of a combination of additives consisting of:

1. 35% of a dispersing agent based on an alkenylsuccinimide, obtained by reacting a succinic anhydride substituted by a polyisobutene (number of carbon atoms between 50 and 60) with triethylenetetramine (see U.S. Pat. No. 3,862,981), 2. 15% of a detergent based on a neutral calcium salt of a sulphone acid, and 3. 50% of a detergent based on a calcium alkylphenate, of which the alkyl radical contains 12 carbon atoms and of which the total basic number is greater than 200 mg. of potassium hydroxide per gram.

The mechanical properties of this resulting lubricating composition were tested on a 4-ball machine according to standard specification ASTM D 2783-69 T. This test gives the scar diameter in mm. under a seizure load of 70, 100 and 120 kg., as well as the welding load in kg.

The oxidation resistance of this composition was evaluated by means of the Mobil oxidation test which consists of oxidizing 33 g. of oil containing the additives by heating the oil to 160° C. for 40 hours in the presence of oxidation catalysts (Pb-Al-Cu-Fe) under an air flow of 13.9 liters per hour, and measuring the increase in viscosity at 37.8° C. (100° F.) of the oxidized oil relative to the fresh oil.

Comparable tests were carried out on compositions in which the product of Example 1 was replaced by the same amount of one of the following additives:

1. additive A, based on a mixture of zinc alkyldithiophosphates wherein the alkyl radicals contain from 4 to 6 carbon atoms, 2. additive B, based on 2,5-bis-(octyldithio)-thiadiazole, 3. additive C, based on sulphurized dodecylphenol, and 4. Additive D, consisting of 7-butylmethyldithiolthione.

The results of all these tests are shown in Table I, below.

It was found, according to this Table, that the composition based on 5-butylthio-4-methyl-1,2-dithiol-3-thione has a very good general level of performance as regards its mechanical properties and these performance characteristics were retained well in spite of the oxidation treatment.

The anti-oxidant properties are also valuable.

EXAMPLE 16

Lubricating compositions were prepared by adding 1% of 5-n-butylthio-4-methyl-1,2-dithiol-3-thione to the following different lubricating oils:

1. an SAE 30 oil, 2. a 100 N oil, 3. a synthetic base based on an ester of dodecanedicarboxylic acid with C$_9$-oxo-alcohols, having a viscosity of 3 cst at 98.9° C. (210° F.) and a viscosity index of 150.

These compositions were tested in accordance with the methods indicated in the preceding example.

The results of these tests are shown in Table II, below.

It was found that these compositions have a very good general level of performance and that the anti-oxidant properties are particularly valuable in the case of the ester.

EXAMPLE 17

Lubricating compositions were prepared by adding 0.2 to 5% of 5-n-butylthio-4-methyl-1,2-dithiol-3-thione to a 100 N oil.

Comparative compositions are also prepared by adding 1% of additive A or of additive C (defined in Example 15) to the same 100 N oil. These compositions were tested in accordance with the methods described in Example 15. The results of these tests are shown in Table III, below.

It was found that:

1. the compositions which form the subject of the invention have a very good general level of performance as regards their mechanical properties, even at a very low concentration of additive, 2. the compositions which form the subject of the invention retain their properties even after oxidation, and 3. 5-n-butylthio-4-methyl-1,2-dithiol-3-thione is an anti-oxidant comparable with the zinc dialkyldithiophosphates.

EXAMPLE 18

Lubricating compositions were prepared by adding to each 1% of one of the products obtained in Examples (Experiments) 2 to 14 to a 100 N oil. These compositions were tested in accordance with the methods indicated in Example 15.

Comparable tests are carried out on the following compositions;

1. a 100 N oil + 1% of the additive A defined in Example 15, and 2. a 100 N oil + 1% of zinc dodecylphenyldithiophosphate (additive E).

The results of all of these tests are shown in Table IV, below.

This Table shows that all the compositions which form the subject of the invention and contain derivatives of 1,2-dithiol-3 -thione or 1,2-dithiol-3-one carrying a 5-alkylthio or 5-alkarylthio substituent have a very good general level of performance as regards mechanical properties, and that these properties are preserved in spite of oxidation.

EXAMPLE 19

A lubricating composition (I) was prepared, which contains 93% of a refined oil of viscosity characteristic 20 W 40 and 7% of a combination of additives consisting of:

1. 30% of a detergent based on calcium alkylphenate, of which the alkyl radical contains 12 carbon atoms and of which the TBN is greater than 200 mg., 2. 20% of a detergent based on a magnesium sulphonate, with a TBN greater than 200 mg., 3. 35% of a dispersing agent based on an alkenylsuccinimide obtained by reacting a succinic anhydride substituted by a polyisobutene (number of carbon atoms between 50 and 60) with triethylenetetramine, and 4. 15% of a mixture of zinc alkyldithiophosphates of which the alkyl radicals contain from 4 to 6 carbon atoms.

Compositions II and III were also prepared, by adding to composition I, respectively, 0.2% by weight of 5-t-butylthio-4-chloro-1,2-dithiol-3-one (composition II) and 0.2% by weight of 5-n-butylthio-4-methyl-1,2-dithiol-3-thione (composition III).

Compositions I, II and III were subjected to the CLR-L 38 engine test for 40 hours.

The results obtained are shown in Table V, below.

TABLE I

| Additive tested | Mechanical Properties | | | | | Oxidation increase in viscosity, 40 hours at 160° C |
|---|---|---|---|---|---|---|
| | Before oxidation | | | | After oxidation | |
| | Scar in mm Seizure | | | Welding load in kg | Seizure | |
| | 70 kg | 100 kg | 120 kg | | 100 kg | |
| Product from Experiment 1 | | 0.50 | 0.80 | 400 | 2.0 | 15% |
| A | | 0.45 | 0.70 | 250 | 2.0 | 5% |
| B | | 0.50 | 0.73 | 400 | 2.3 | 11% |
| C | 0.43 | 1.80 | | 250 | 2.2 | 46% |
| D | | 0.48 | 1.20 | 400 | 2.4 | 12% |

TABLE II

| Composition | Mechanical properties | | | | | Oxidation increase in viscosity, 40 hours at 160° C |
|---|---|---|---|---|---|---|
| | Before oxidation | | | | After oxidation | |
| | Scar in mm Seizure | | | Welding load in kg | Seizure | |
| | 70 kg | 100 kg | 120 kg | | 100 kg | |
| Pure SAE 30 | 2.1 | | | 250 | 2.6 | 20% |
| SAE 30 + 1% of additive | 0.41 | 0.50 | 1.10 | 400 | 1.8 | 11% |
| 100 N + 1% of additive | 0.45 | 0.50 | 1.20 | 300 | 2.0 | 4% |
| Pure ester | 1.90 | 2.6 | | >250 | 2.2 | 200% |
| Ester + 1% of additive | | 0.60 | 0.75 | 300 | 2.2 | 100% |

TABLE III

| Composition | Mechanical properties | | | | | Oxidation increase in viscosity, 40 hours at 160° C |
|---|---|---|---|---|---|---|
| | Before oxidation | | | | After oxidation | |
| | Scar in mm Seizure | | | Welding load in kg | Seizure | |
| | 70 kg | 100 kg | 120 kg | | 100 kg | |
| 100 N + 0.2% of the additive of the invention | 0.50 | 1.3 | | 250 | 2.6 | 6% |
| 100 N + 0.5%  " | 0.45 | 1.0 | | 250 | 2.4 | 4% |
| 100 N + 1%  " | 0.45 | 0.50 | 1.20 | 300 | 2.0 | 4% |
| 100 N + 3%  " | 0.45 | 0.50 | 0.70 | 300 | 0.8 | 4% |
| 100 N + 5%  " | 0.45 | 0.50 | 0.70 | 300 | 0.7 | 4% |
| 100 N + 1% A | | 0.5 | 2.00 | 250 | 2.2 | 2% |
| 100 N + 1% C | 2.00 | 2.8 | | 250 | <2.9 | 25% |

TABLE IV

| Additive tested | Mechanical properties | | | | | Oxidation increase in viscosity, 40 hours at 160° C |
|---|---|---|---|---|---|---|
| | Before oxidation | | | | After oxidation | |
| | Scar in mm Seizure | | | Welding load in kg | Seizure | |
| | 70 kg | 100 kg | 120 kg | | 100 kg | |
| Product of Expt. 2 | | 0.50 | 1.30 | 250 | 1.90 | 6% |
| Product of Expt. 3 | 0.40 | 0.60 | 2.10 | 250 | 2.20 | 10% |
| Product of Expt. 4 | 0.60 | 1.30 | | 250 | 2.50 | 16% |
| Product of Expt. 5 | | 0.50 | 1.20 | 300 | 1.80 | 8% |
| Product of Expt. 6 | 0.60 | 1.40 | | 250 | 2.00 | 16% |
| Product of Expt. 7 | | 0.40 | 0.70 | 350 | 1.70 | 9% |
| Product of Expt. 8 | 0.40 | 0.60 | 2.50 | 300 | 1.90 | 11% |
| Product of Expt. 9 | 0.50 | 1.20 | | 300 | 2.10 | 13% |
| Product of Expt. 10 | 0.40 | 0.60 | 2.00 | 250 | 2.00 | 7% |
| Product of Expt. 11 | 0.60 | 1.40 | | 250 | 2.10 | 15% |
| Product of Expt. 12 | | 0.40 | 0.70 | 350 | 1.70 | 13% |
| Product of Expt. 13 | | 0.40 | 0.70 | 400 | 1.90 | 13% |
| Product of Expt. 14 | 0.40 | 0.70 | 1.80 | 300 | 2.10 | 19% |
| Product of A | | 0.5 | 2.00 | 150 | 2.2 | 2% |
| Product of B | 0.60 | 0.80 | 2.50 | 250 | 2.8 | 24% |
| Product of C | 1.80 | 2.40 | | 200 | 2.5 | 3% |

TABLE V

|  | COMPOSITION I | COMPOSITION II | COMPOSITION III |
|---|---|---|---|
| Varnish rating | 59.0 | 59.1 | 59.0 |
| Sludge rating | 59.1 | 59.2 | 59.1 |
| Bearing weight loss in mg | 60 | 30 | 29 |
| Change in viscosity of the oil after 40 hours | −4% | −12% | −9% |

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A novel lubricating composition comprising a major proportion of at least one lubricating oil and between about 0.2 and 10% by weight of at least one additive which is a derivative of a 1,2-dithiol-3-thione or a 1,2-dithiol-3-one, characterized in that the said derivative has the formula:

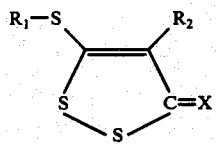

in which formula $R_1$ is a member selected from the class consisting of alkyl and alkylaromatic hydrocarbon radicals, $R_2$ is a member selected from the class consisting of a hydrogen atom, alkyl radicals, a halogen atom, or a carboxyalkyl radical COOR in which R is an alkyl radical containing from about 1 to 12 carbon atoms, $R_1$ and $R_2$ together having a total of from about 3 to 24 carbon atoms when $R_2$ is a hydrogen atom, an alkyl or carboxyalkyl radical, and $R_1$ having from about 2 to 22 carbon atoms when $R_2$ is a halogen atom, and X is a sulphur or oxygen atom, but when an oxygen atom, $R_2$ is a halogen atom.

2. A novel lubricating composition according to claim 1, characterized in that $R_1$ and $R_2$ together have a total of from about 5 to 24 carbon atoms when $R_2$ is an alkyl or carboxyalkyl radical, $R_1$ contains from about 5 to 19 carbon atoms when $R_2$ is a hydrogen atom and $R_1$ has from about 3- to 13 carbon atoms when $R_2$ is a chlorine atom.

3. A novel lubricating composition according to claim 1, characterized in that the derivative of the 1,2-dithiol-3-thiones or 1,2-dithiol-3-ones is a member selected from the class consisting of: 5-n-butylthio-4-methyl-1,2-dithiol-3-thione, 5-hepthylthio-4-methyl-1,2-dithiol-3-thione, 5-dodecylthio-4-methyl-1,2-dithiol-3-thione, 5-dodecylbenzylthio-4-neopentyl-1,2-dithiol-3-thione, 5-n-pentylthio-4-H-1,2-dithiole-3 -thione, 5-para-dodecylbenzylthio-4-H-1,2-dithiol-3-thione, 5-t-butylthio-4-chloro-1,2-dithiol-3-thione, 5-dodecylthio-4-chloro-1,2-dithiol-3-thione, 5-p-methylbenzylthio-4-chloro-1,2-dithio-3-thione, 5-n-hexylthio-4-carbonhyxoxy-1,2-dithio-3-thione, 5-hexylbenzylthio-4-carbohexoxy-1,2-dithiol-3-thione, 5-t-butylthio-4-chloro-1,2-dithiol-3-one, 5-isopropylthio-4-chloro-1,2-dithiol-3-one and 5-hexylbenzylthio-4-chloro-1,2-dithio-3-one.

4. A novel lubricating composition according to claim 1 wherein the said derivative is present in an amount of between about 0.2 and 5% by weight.

5. A novel composition according to claim 1 wherein the lubricating oil is a member of the class consisting of natural oils synthetic oils, and mixtures thereof of viscosity between about 20.6 and 541 centistokes at 37.8° C.

* * * * *

UNITED STATES PATENT AND TRADEMARK OFFICE
CERTIFICATE OF CORRECTION

PATENT NO. : 4,042,514

DATED : August 16, 1977

INVENTOR(S) : Francois Giolito et al.

It is certified that error appears in the above–identified patent and that said Letters Patent are hereby corrected as shown below:

Col. 3, line 42, delete "rusulting" and replace with -- resulting --.

Col. 3, line 50, delete "6°" and replace with -- 60° --.

Col. 3, line 60, delete "and" and replace with -- an --.

Col. 5, line 5, delete "5-butylthio-" and replace with -- 5-t-butylthio- --.

Col. 7, line 11, delete "lubrocating" and replace with -- lubricating --.

Col. 7, line 57, delete "5-butylthio-" and replace with -- 5-n-butylthio- --.

Table IV, fifth column, third line from bottom, delete "150" and replace with -- 250 --.

Col. 12, line 29, delete "carbonhyxoxy" and replace with -- carbohexoxy --.

Signed and Sealed this

*Fifteenth* Day of *November 1977*

[SEAL]

*Attest:*

RUTH C. MASON
*Attesting Officer*

LUTRELLE F. PARKER
*Acting Commissioner of Patents and Trademarks*